United States Patent [19]
Clemens et al.

[11] Patent Number: 5,531,694
[45] Date of Patent: Jul. 2, 1996

[54] NEEDLE RETRACTION SYSTEM

[76] Inventors: Anton H. Clemens, 5854 Schumann Dr., Madison, Wis. 53711; Victor M. Haughton, 1071 Waterville Rd., Oconomowoc, Wis. 53066

[21] Appl. No.: 398,543

[22] Filed: Mar. 6, 1995

Related U.S. Application Data

[63] Continuation-in-part of Ser. No. 114,472, Aug. 31, 1993, Pat. No. 5,395,337.

[51] Int. Cl.⁶ .................................................. A61M 5/00
[52] U.S. Cl. ................................................ 604/110; 604/195
[58] Field of Search ..................................... 604/110, 195, 604/218, 220, 263

[56] References Cited

U.S. PATENT DOCUMENTS

| | | |
|---|---|---|
| 2,722,215 | 11/1955 | Dahlgren. |
| 2,841,143 | 7/1958 | Bertram. |
| 3,825,003 | 7/1974 | Kruck. |
| 4,009,716 | 3/1977 | Cohen. |
| 4,573,976 | 3/1986 | Sampson et al.. |
| 4,664,259 | 5/1987 | Landis. |
| 4,676,783 | 6/1987 | Jagger et al.. |
| 4,747,831 | 5/1988 | Kulli. |
| 4,767,413 | 8/1988 | Haber et al.. |
| 4,826,484 | 5/1989 | Haber et al.. |
| 4,838,869 | 6/1989 | Allard. |
| 4,874,382 | 10/1989 | Lindemann et al.. |
| 4,955,870 | 9/1990 | Ridderheim et al.. |
| 4,994,034 | 2/1991 | Botich et al.. |
| 5,000,736 | 3/1991 | Kaufhold, Jr. et al.. |
| 5,180,369 | 1/1993 | Dysarz. |
| 5,211,629 | 5/1993 | Pressly et al.. |
| 5,338,304 | 8/1994 | Adams ................................. 604/110 |
| 5,407,436 | 4/1995 | Toft et al. ............................. 604/195 |

FOREIGN PATENT DOCUMENTS

| | | |
|---|---|---|
| 0347742 | 12/1989 | European Pat. Off.. |
| 2675999 | 4/1991 | France. |
| 3925834 | 2/1991 | Germany. |
| WO91/03269 | 3/1991 | WIPO. |
| WO91/11883 | 7/1992 | WIPO. |
| WO93/07923 | 4/1993 | WIPO. |

*Primary Examiner*—John D. Yasko
*Attorney, Agent, or Firm*—Andrus, Sceales, Starke & Sawall

[57] ABSTRACT

A retractable needle medical assembly includes a barrel and a plunger assembly defining an internal passageway. A sleeve is mounted to the barrel and extends into the internal passageway defined by the plunger assembly. An actuator member, in the form of an actuator tube, is mounted within the sleeve toward its rearward end, and includes a trigger which can either be manually engaged by the user or engaged by the plunger when the plunger is in its full-forward position relative to the barrel. A hub is received within the sleeve passage, and a spring bears against the hub so as to urge the hub to a rearward, retracted position. The actuator tube engages the hub so as to maintain the hub in a forward position, and a needle assembly consisting of a needle and a head is engaged with the hub by the user prior to operation of the assembly. Depression of the trigger results in movement of the actuator tube to disengage the actuator tube from the hub, so as to allow the spring to propel the hub, and thereby the needle assembly, rearwardly to retract the needle into the sleeve passage and to prevent accidental contact therewith. The needle retraction system may be incorporated into a medical device such as a syringe, or into a system for collecting blood or other body fluids from a patient.

17 Claims, 7 Drawing Sheets

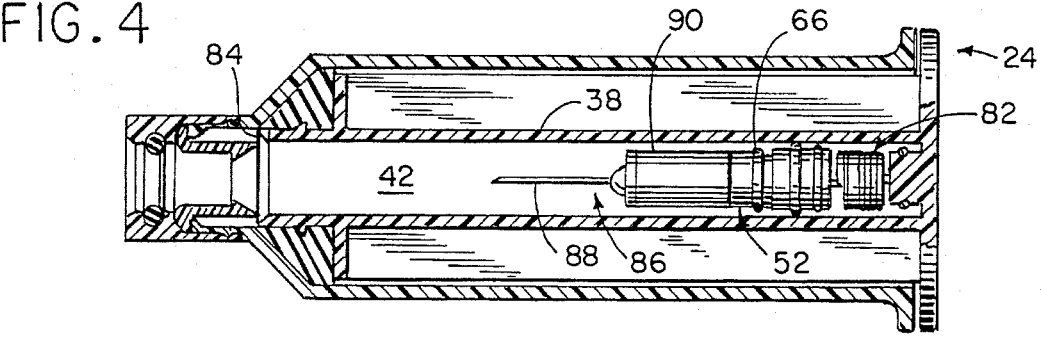
FIG. 4
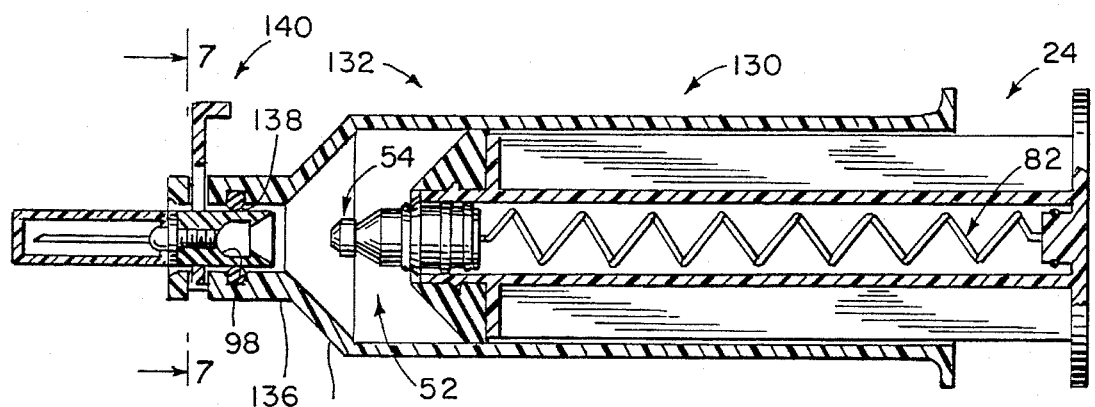
FIG. 5
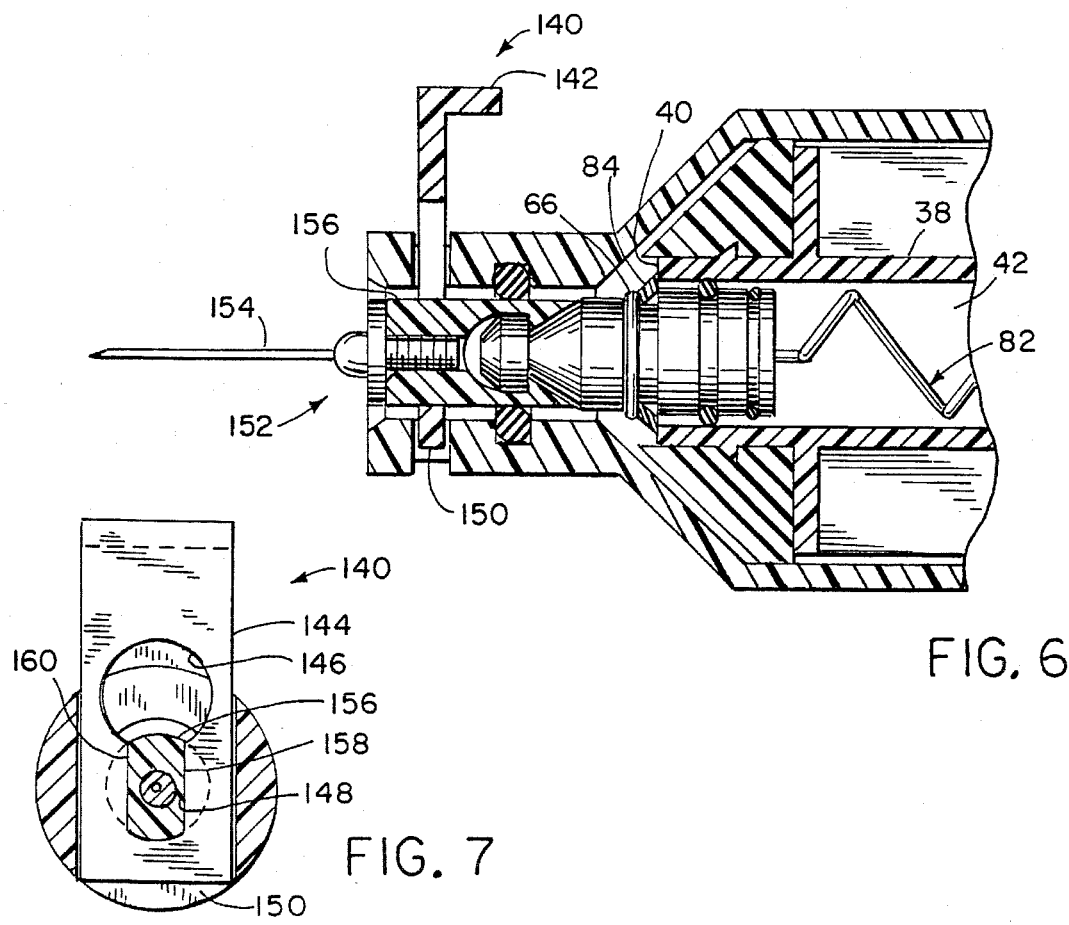
FIG. 6
FIG. 7

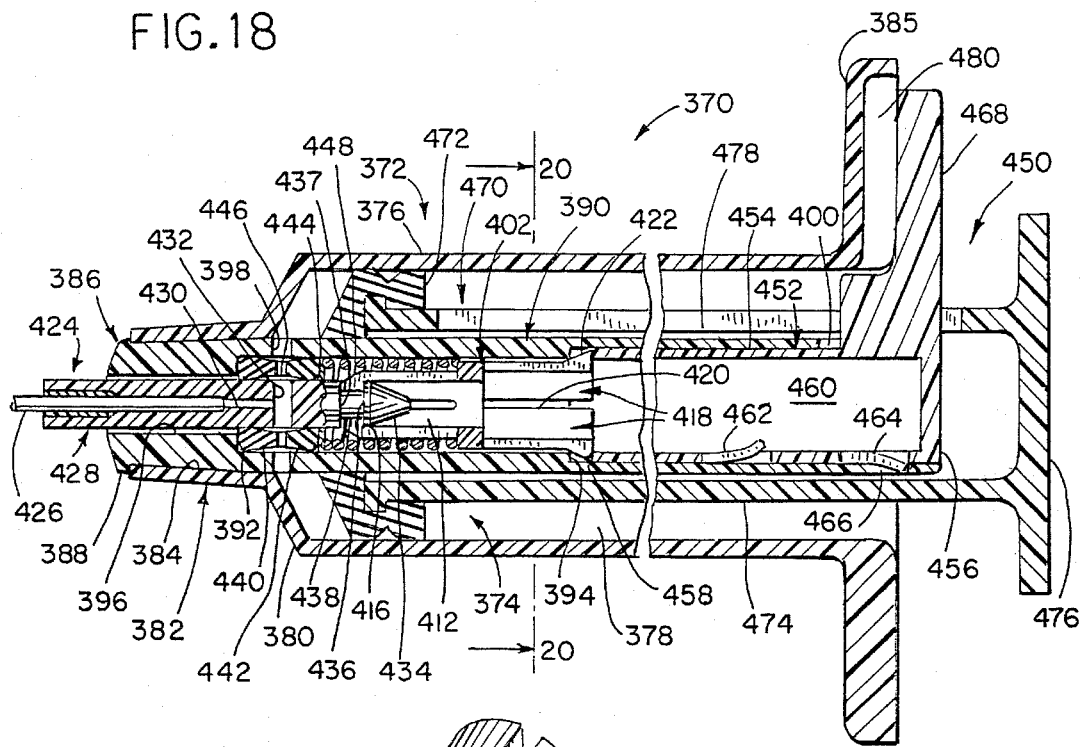
FIG. 18
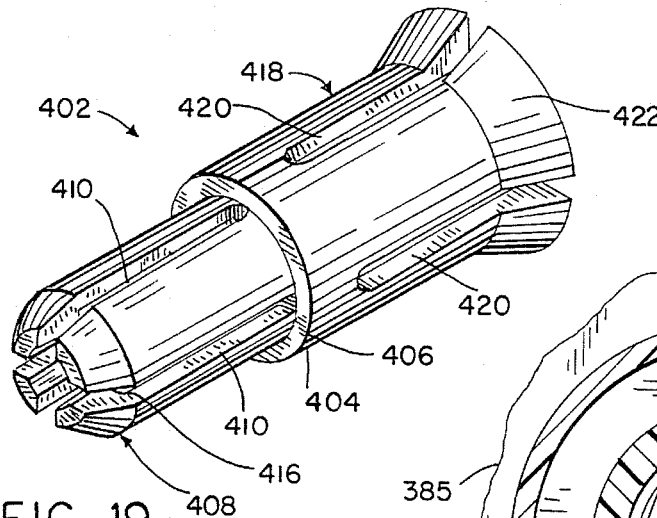
FIG. 19
FIG. 20

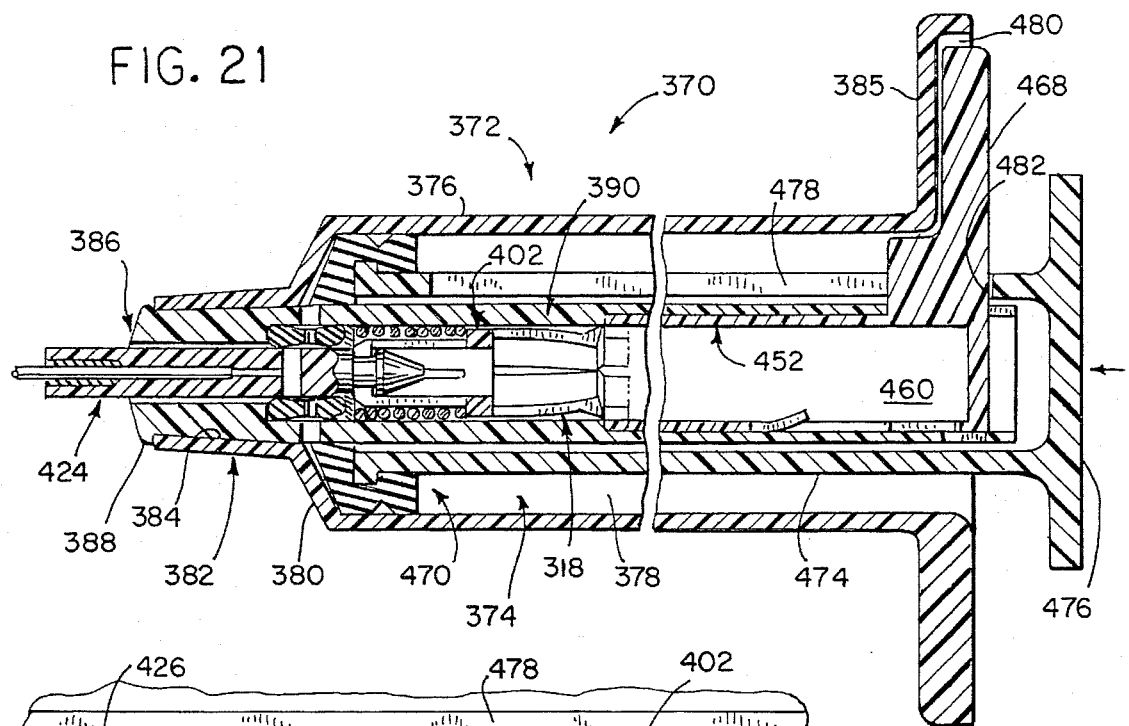
FIG. 21
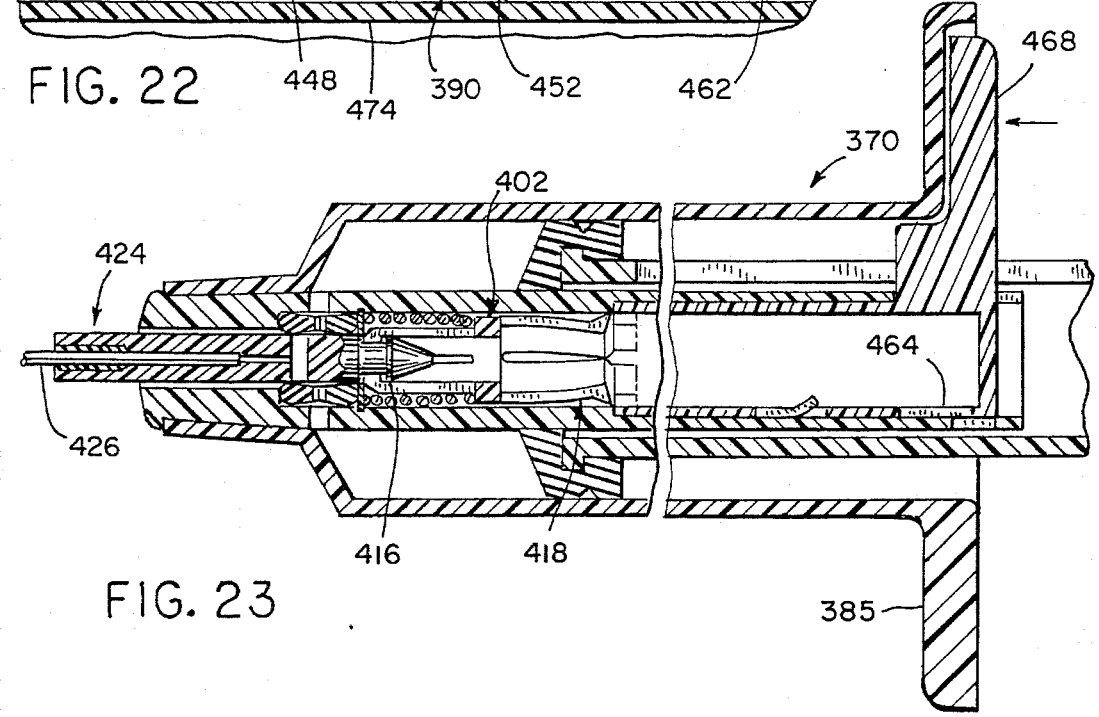
FIG. 22
FIG. 23

1

NEEDLE RETRACTION SYSTEM

CROSS-REFERENCE TO RELATED APPLICATIONS

This application is a continuation-in-part of application Ser. No. 08/114,472, filed Aug. 31, 1993, now U.S. Pat. No. 5,395,337, issued Mar. 7, 1995.

BACKGROUND AND SUMMARY

This invention pertains to a syringe or the like for injecting or withdrawing a fluid into or from a patient, and more particularly to a needle retraction system for disarming such a device after use.

The hazards associated with accidental needle sticks are well known. Many issued patents disclose syringes or the like having mechanisms for retracting or otherwise enclosing a syringe needle after use, to prevent accidental contact with the needle.

It is an object of the present invention to provide an improved needle retraction mechanism for use with a syringe or the like for preventing accidental needle sticks. It is a further object of the invention to provide a needle retraction mechanism which is relatively simple in its construction and operation.

In accordance with one aspect of the invention, a syringe assembly includes a barrel having an internal cavity and defining a first closed end and a second open end. A plunger is mounted for longitudinal sliding movement within the barrel cavity. The plunger includes a longitudinal internal passageway. A first end of the plunger is disposed within the barrel cavity, and a second end of the plunger is disposed exteriorly of the barrel. The internal passageway opens onto the first end of the plunger. A retraction member is releasably engaged with the plunger, and is located within the internal passageway at the first end of the plunger. Bias means is provided for urging the retraction member into the passageway toward the second end of the plunger. In one form, the bias means consists of a spring interconnected between the retraction member and the plunger. A needle assembly consists of a needle engageable with a hub member, with the hub member including a passage establishing communication between the barrel cavity and the needle lumen. The needle is selectively engageable with the hub member such that the needle is engaged just prior to use of the syringe assembly. This enables the operator of the syringe assembly to select the appropriately sized needle according to the application in which the syringe assembly is used. In one form, the needle includes a head having external threads engageable with internal threads formed in the passage of the hub member. This enables the operator to remove the needle, if already in place, and replace it with a different needle if desired. In another form, the needle head includes a frustoconical cam surface defining a shoulder, and the hub passage is shaped so as to receive the frustoconical head of the needle. The hub member further includes resilient fingers having hooks at their forward ends, and the fingers are forced outwardly during insertion of the head into the needle passage. The fingers return to their original position to engage the shoulder defined by the needle head after placement of the needle head into the passage, so as to engage the needle with the hub member. In this arrangement, the needle cannot be selectively removed from the hub member after connection thereto.

In accordance with another aspect of the invention, engagement means may be interposed between the retraction member and the hub member for engaging the retraction member with the hub member upon movement of the plunger toward the first end of the barrel. A selectively actuable release mechanism maintains the retraction member in position within the plunger passageway at the first end of the plunger against the force of the bias means prior to engagement of the retraction member with the hub member during movement of the plunger toward the first end of the barrel. The release mechanism functions to release engagement of the retraction member with the plunger after engagement of the retraction member with the hub member. A releasable retainer mechanism is interposed between the hub member and the barrel for releasably engaging the hub member with the barrel. The releasable retainer mechanism is operable to release engagement between the barrel and the hub member, either before or after engagement of the retraction member with the hub member, to provide withdrawal of the hub member and needle into the passageway of the plunger after use of the syringe.

In accordance with yet another aspect of the invention, the plunger longitudinal internal passageway may be defined by a sleeve engaged with the closed end of the barrel. The sleeve includes a first end engaged with the closed end of the barrel and a second end spaced therefrom, preferably extending outwardly of the open end of the barrel. The hub member is disposed within the sleeve adjacent its first end, and bias means, such as in the form of a spring, is interposed between the hub member and the sleeve for biasing the hub member toward the second end of the sleeve. A releasable retainer mechanism is interposed between the hub member and the sleeve. The releasable retainer mechanism is movable between an engaged position in which the hub member is maintained in a fixed position adjacent the first end of the sleeve, and a disengaged release position. An actuator member is interconnected with the releasable retainer mechanism for selectively moving the releasable retainer mechanism to its release position in response to actuation by the operator to provide withdrawal of the hub member, and thereby the needle, into the sleeve to disarm the syringe assembly when desired. The actuator is located adjacent the open end of the barrel, and is engageable by the operator's thumb or finger so as to provide movement of the releasable retainer mechanism to its release position at any time during movement of the plunger. This enables the operator to disarm the syringe assembly whether or not all of the fluid has been ejected from the barrel. Once the hub member is moved to the second end of the sleeve by operation of the bias means, the bias means maintains the hub member in position therein to prevent subsequent reuse of the syringe assembly. Preferably, a one-way stop is provided in the sleeve to engage the hub member to prevent it from moving toward the first end of the sleeve after the hub member has passed by the stop member during disarming of the syringe assembly.

In accordance with further aspects of the invention, the hub member may be received within a sleeve which is engageable with the exterior of the barrel for engaging the hub member with the first end of the barrel. Further, the releasable retainer mechanism may be actuated automatically in response to movement of the plunger. In this form of the invention, the releasable retainer mechanism may take the form of a base disposed between the sleeve and the first end of the barrel, mounted to the barrel by engagement of the sleeve with the barrel. A series of flexible retaining fingers extend from the base and releasably engage the hub member. Movement of the plunger toward the first end of the barrel engages the retraction member with the fingers, which functions to flex the fingers outwardly to release engagement of the hub member with the barrel. Alternatively, the releasable retainer mechanism may take the form of a manually operated actuator member engaged between the barrel and the hub member, to retract the needle after use upon manual actuation by the user. The manually operated actuator member is movable between a retaining position and a release position, and functions to retain the hub member in position relative to the barrel when in its retaining position against the force of the biasing means when the retraction member is engaged with the hub member, and to release engagement of the hub member with the barrel when in its release position to allow the bias means to withdraw the retraction member, the hub member and the needle into the passageway. The first closed end of the barrel terminates in one or more walls defining a restricted passage within which the hub member is disposed when engaged with the barrel. The manually operated actuator member is engaged with the hub member, and is movably mounted to the one or more walls defining the restricted passage between its retaining position and its release position.

In either the manual or automatic versions summarized above, the bias means may take the form of a spring, as noted previously, or alternatively may be in the form of a vacuum provided in the passageway for urging the retraction member toward the second end of the passageway.

The selectively actuable release mechanism may be in the form of peripheral ridge structure provided on the retraction member, and a retaining ring interposed between the peripheral ridge structure and a peripheral end wall defined by the passageway at the first end of the plunger. Movement of the plunger toward the first end of the barrel results in the peripheral end wall forcing the retaining ring over the peripheral ridge structure, to release engagement of the retainer member with the plunger. In this manner, the retraction member functions to withdraw the hub member into the internal passageway defined by the plunger under the influence of the biasing means after the releasable retainer mechanism is operated to release engagement between the barrel and the hub member.

In accordance with yet another aspect of the invention, the releasable retainer mechanism includes an actuator movably mounted to the sleeve and a trigger mounted to the actuator. The actuator is movable within the sleeve between a retaining position in which the actuator is engageable with the hub member for retaining the hub member in its forward position, and a release position in which engagement between the actuator and the hub member is released. The trigger extends laterally outwardly toward the rearward end of the syringe through a slot formed in a wall of the plunger. Preferably, the trigger is disposed adjacent and rearwardly of a flange provided at the rearward end of the barrel. The trigger is actuable by the user at any time regardless of the position of the plunger relative to the barrel by manual engagement of the trigger by the user, or is engageable by the plunger when the plunger attains a predetermined position relative to the barrel, e.g. as the plunger reaches its full forward position. In either instance, the trigger is operable to move the actuator to its release position so as to release engagement with the hub member, and to enable the hub member to be propelled rearwardly under the influence of the bias means so as to withdraw the needle into the internal passage defined by the sleeve.

In accordance with still another aspect of the invention, the hub member includes one or more flexible retainers engageable with the actuator for retaining the hub member in its forward position when the actuator is in its retaining position. The flexible retainers are moved out of engagement with the actuator upon movement of the actuator to its release position so as to release engagement of the hub member with the actuator. Each flexible retainer includes a ramped actuator surface toward its rearward end, and the sleeve defines an internal shoulder which engages the actuator surfaces as the hub member is moved forwardly by movement of the actuator to its release position. The ramped actuator surfaces function to flex the one or more flexible retainers inwardly until the retainers are moved out of engagement with the forward end of the actuator. The actuator is preferably in the form of a tubular member defining an internal passage into which the hub member is propelled under the influence of the bias means so as to draw the needle into the internal passage defined by the sleeve.

The invention further contemplates a method of disarming a syringe after use, substantially in accordance with the foregoing summary.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings:

FIG. 4 is a view similar to FIG. 1, showing the needle assembly withdrawn into the internal passageway of the plunger under the influence of the biasing means for disarming the syringe after use;

FIG. 5 is a view similar to FIG. 1, showing an alternative embodiment of the invention in which a manually operable actuator member retains the hub member of the needle assembly in engagement with the first end of the barrel;

FIG. 6 is an enlarged partial section view, similar to FIG. 2, showing the syringe assembly of FIG. 5 in a position in which the retraction member is engaged with the hub member of the needle assembly;

FIG. 7 is a section view taken along line 7—7 of FIG. 5;

FIG. 18 is a longitudinal cross-sectional view of a syringe incorporating yet another embodiment of the needle retraction apparatus and method of the invention, showing the needle assembly and hub member retained in their extended position;

FIG. 19 is an isometric view showing the hub member incorporated in the needle retraction apparatus of FIG. 18;

FIG. 20 is a partial section view taken along line 20—20 of FIG. 18;

FIG. 21 is a view similar to FIG. 18, showing actuation of the needle retraction apparatus for moving the releasable retainer mechanism to its release position upon movement of the plunger to its full-forward position;

FIG. 22 is a partial longitudinal cross-sectional view of the needle retraction apparatus of FIG. 21, showing the hub member and needle assembly moved rearwardly under the influence of the bias means so as to draw the needle into the internal passage defined by the sleeve; and FIG. 23 is a view similar to FIG. 21, showing engagement of the trigger when the plunger is not moved to its full-forward position so as to move the releasable retainer mechanism to its release position even when the full contents of the syringe have not been ejected.

DETAILED DESCRIPTION OF THE INVENTION

Figure 1:
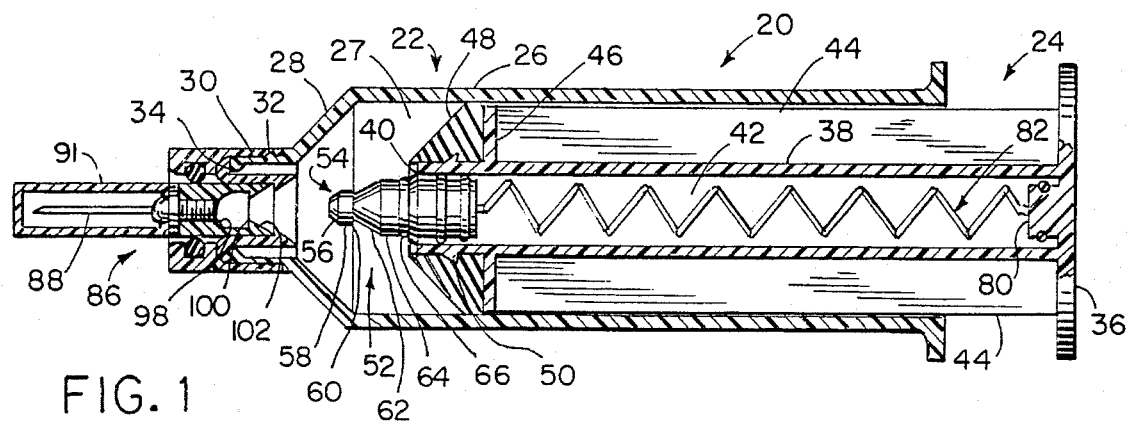
FIG. 1 is a longitudinal cross-sectional view of a syringe incorporating the needle retraction apparatus and method of the invention, showing the position of the plunger prior to engagement of the retraction member with the hub member during movement of the plunger toward the first end of the barrel.

FIG. 1 illustrates a syringe assembly 20 which generally includes a barrel 22 and a plunger 24. Barrel 22 includes a cylindrical side wall 26 defining an internal cavity 27, and a frustoconical wall 28 located between side wall 26 and end wall 30. End wall 30 includes a circumferential rib 32, and terminates in a forward end 34.

Plunger 24 includes a thumb plate 36 and a forwardly extending cylindrical wall 38 which terminates in a forward end 40. Cylindrical wall 38 defines an internal passageway 42. Ribs 44 extend outwardly from cylindrical wall 38, and extend between thumb plate 36 and a ring 46. A resilient plunger head 48 is mounted to the forward end of plunger 24. Head 48 defines a passage within which the end portion of cylindrical wall 38 is received. A groove is formed in the internal passageway of head 48, for receiving a peripheral rib 50 located toward the forward end of cylindrical wall 38. With this arrangement, head 48 is assembled onto plunger 24 by means of a rearward push-on motion, to engage the groove provided in the internal passage through head 48 with rib 50 and to abut the rearward surface of head 48 with the forward surface of ring 46, to retain head 48 in position on plunger 24. In a manner as is known, the outer peripheral edge of head 48 provides a fluid-tight seal with the inner surface of syringe wall 26.

Figure 2:
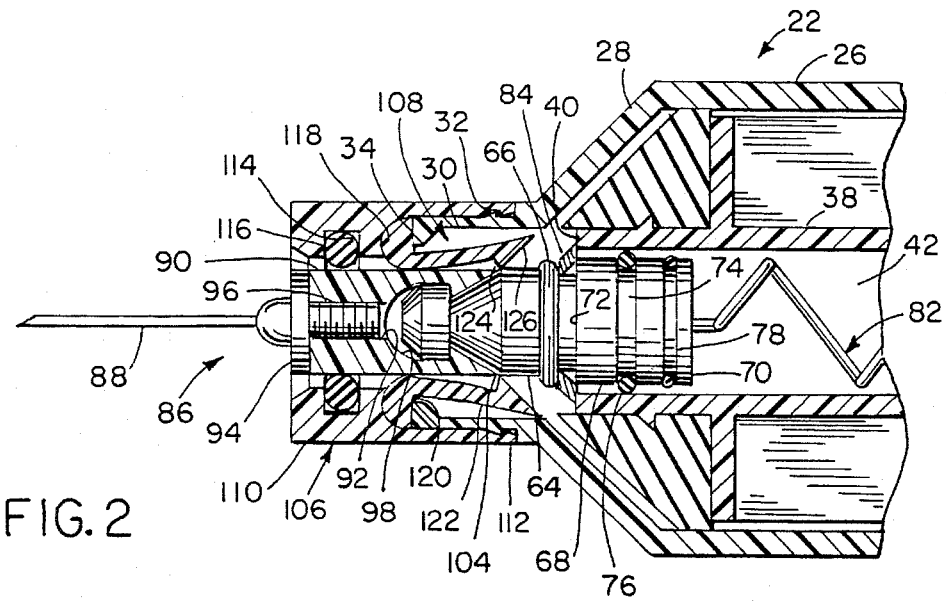
FIG. 2 is a partial longitudinal section view of the end portion of the syringe of FIG. 1, showing engagement of the retraction member with the hub member of the needle assembly.

A retraction member, shown generally at 52, is interconnected with plunger 24 at the forward end of cylindrical wall 38. The forward end of retraction member 52 defines a head 54 having an angled leading surface 56, a side surface 58 and a circumferential shoulder 60. Rearwardly of shoulder 60, head 52 defines an angled actuator surface 62 and a side surface 64. Side surface 64 is provided with peripheral ridge structure, in the form of a ring 66 engaged within a groove formed in side surface 64. Referring to FIG. 2, retraction member 52 rearwardly of side surface 64 defines an enlarged rear portion including a side wall 68, a rear end surface 70 and a shoulder 72 disposed between side surfaces 64 and 68. A groove 74 is formed in side surface 68, and an O-ring 76 is seated within groove 74 for providing a fluid-tight seal between plunger passageway 42 and internal cavity 27 defined by barrel 22. A groove 78 is formed in retraction member side wall 68 rearwardly of groove 74.

Referring to FIG. 1, a boss 80 is formed integrally with plunger thumb plate 36, extending forwardly into passageway 42. A spring 82 extends between boss 80 and retraction member 52. Spring 82 is connected at its rearward end to boss 80 by means of a groove formed in the side wall of boss 80. At its forward end, spring 82 is engaged within groove 78.

A retaining ring 84 is positioned between ring 66 and annular end surface 40 defined by cylindrical wall 38 of plunger 24. Retaining ring 84 is constructed so as to flare outwardly in a rearward direction, so that the forward end of ring 84 is closely engaged with retraction member 52 rearwardly of ring 66. Retaining ring 84 is thus substantially frustoconical in shape, and provides a releasable retaining mechanism for maintaining retraction member 52 in its position as shown in FIGS. 1 and 2 against the force exerted on retraction member 52 by spring 82, tending to urge retraction member 52 rearwardly within passage 42.

Referring to FIGS. 1 and 2, a needle assembly 86 is located at the forward end of barrel 22. Needle assembly 86 includes a needle 88 defining a lumen, and a hub 90 to which needle 88 is mounted. In FIG. 1, needle 88 is shown enclosed by a conventional needle sheath 91. As shown in FIG. 2, hub 90 defines an internally threaded passage 92. Needle 88 extends forwardly from a flange 94, and an externally threaded hollow stud 96 extends rearwardly from flange 94. Stud 96 is threaded into internally threaded passage 92 of hub 90, to mount needle assembly 86 to hub 90.

Needle 88 is manually engaged with hub 90 just prior to use of syringe assembly 20 by threading stud 96 into threaded passage 92 of hub 90. This way, a user can stock several different sizes of needle 88, and select the appropriate needle size for the particular application.

Hub 90 includes a cavity 98 in communication with passage 92. A shoulder 100 defines a narrowed entryway into cavity 98. A tapered wall 102 extends rearwardly from shoulder 100, defining a rearwardly facing opening in hub 90. Tapered wall 102 terminates in a rearward annular end 104 (FIG. 2).

As a means for engaging needle assembly 86 with barrel 22, a sleeve 106 and a retainer member, shown generally at 108, are mounted to barrel end wall 30. Sleeve 106 defines a thickened forward portion 110 and a rearward portion 112. Rearward portion 112 defines an internal groove within which rib 32 on barrel end wall 30 is received, for mounting sleeve 106 to end wall 30 upon application of a push-on force. Forward portion 110 of sleeve 106 defines an internal groove 114 within which an O-ring 116 is seated. The inner periphery of O-ring 116 engages the outer surface of hub 90, for providing a fluid-tight seal to barrel internal cavity 27.

Sleeve 106 further defines an annular seat 118, which provides a transition between thickened forward portion 110 and rearward portion 112. Seat 118 faces end 34 of barrel end wall 30.

Retainer member 108 consists of a base 120 and a series of resilient fingers 122 extending rearwardly from base 120. Base 120 is sandwiched between seat 118 and end 34 of barrel end wall 30, for fixing retainer member 108 in position relative to barrel 22 and sleeve 106. Each of fingers 122 defines a shoulder 124, which engages annular end 104 defined by hub 90. Each finger 122 further defines a ramped surface 126 located rearwardly of shoulder 124.

In operation, syringe 20 functions as follows. The user first removes sheath 91 to expose needle 88. Needle 88 is inserted into a patient, and liquid contained within barrel cavity 27 is ejected therefrom into the patient by movement of plunger 24 in a right-to-left direction toward hub 90. The liquid passes from barrel cavity 27 into hub cavity 98, through passage 92 and hollow stud 96 into the lumen of needle 88.

As plunger head 48 approaches the inner surface of barrel frustoconical wall 28, retraction member head 54 passes between ramped surfaces 126 of retainer member fingers 122 and tapered wall 102 defined by hub 90, until retraction member head 54 is disposed within hub cavity 98 as shown in FIG. 2. In this position, shoulder 60 defined by retraction member head 54 engages shoulder 100 defined by hub cavity 98, so as to engage retraction member 52 with hub 90, and thereby with needle assembly 86. As head 54 is forced into hub cavity 98, angled actuator surface 62 of retraction member 52 engages ramped surfaces 126 defined by retainer member fingers 122, to deflect fingers 122 outwardly to their position as shown in FIG. 2. When fingers 122 are in this position, engagement between hub 90 and barrel 22 is released. Needle assembly 86 is thus subjected to the rearward bias exerted by spring 82, and is retained in position by retaining ring 84. With plunger 24 in its FIG. 2 position, substantially the entire amount of liquid contained within barrel cavity 27 is ejected therefrom through needle 88. Upon final forward movement of plunger 24 to its position of FIG. 3, retaining ring 84 is inverted and forced over ring 66 mounted to retraction member 52, to release engagement between plunger 24 and retraction member 52. Once retaining ring 84 is moved to its FIG. 3 position, spring 82 functions to withdraw retraction member 52 and needle assembly 86 rearwardly into passage 42, to its position as shown in FIG. 4. With needle assembly 86 in its FIG. 4 position, access to the tip of needle 88 is prevented, to avoid inadvertent contact with needle 88 after use of syringe 20.

Syringe 20 is thus permanently disabled, and needle assembly 86 cannot thereafter be returned to its FIG. 1 position for reuse.

An alternative form of the invention is illustrated in FIGS. 5–7. As shown in FIGS. 5–7, a syringe assembly 130 consists of a barrel 132 and a plunger assembly. The plunger assembly, including retraction member 52, is identical to that disclosed in the embodiment of FIGS. 1–4, and accordingly like reference characters will be used where possible to facilitate clarity.

In the embodiment of FIGS. 5–7, barrel 132 includes a frustoconical wall 134, and a cylindrical end wall 136. An O-ring 138 is seated within an internal groove formed in end wall 136. A manually operable actuator member 140 is engaged with end wall 136. Referring to FIGS. 6 and 7, actuator member 140 includes an engagement surface 142 and a transverse plate portion 144. An opening is formed in plate portion 144. The opening includes a circular upper portion 146 and a slot-like lower portion 148. Actuator member 140 is mounted within a slot 150 formed in barrel end wall 136, between a retaining position as shown in FIGS. 5–7 in which slot-like lower opening portion 148 is aligned with the longitudinal axis of end wall 136, and a release position in which circular upper opening portion 146 is aligned with the longitudinal axis of barrel end wall 136. Actuator member 140 is movable between its retaining and release positions in response to application of a transverse force exerted on actuator member engagement surface 142 in a direction perpendicular to the longitudinal axis of barrel end wall 136.

In the embodiment of FIGS. 5–7, a needle assembly 152 consists of a needle 154 mounted to a hub 156 in the same manner described with respect to needle assembly 86 in the embodiment of FIGS. 1–4. Referring to FIG. 7, needle assembly hub 156 includes a pair of slots 158, 160 which receive plate portion 144 of actuator member 140 adjacent slot-like lower opening portion 148, when actuator member 140 is in its retaining position. With this construction, downward movement of actuator member 140 to its release position moves the material of plate portion 144 out of engagement with slots 158, 160 in hub 156.

Figure 3:
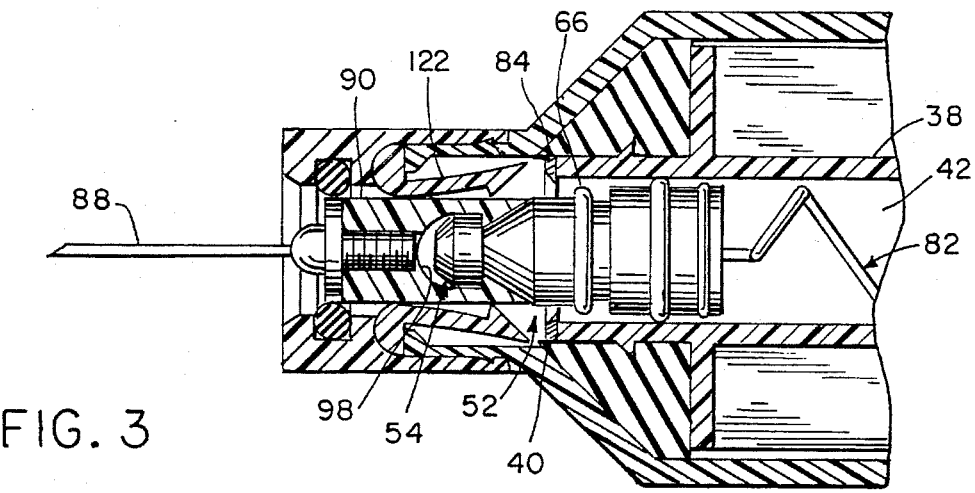
FIG. 3 is a view similar to FIG. 2, showing final movement of the plunger toward the first end of the barrel for releasing engagement between the retraction member and the plunger.
Figure 8:
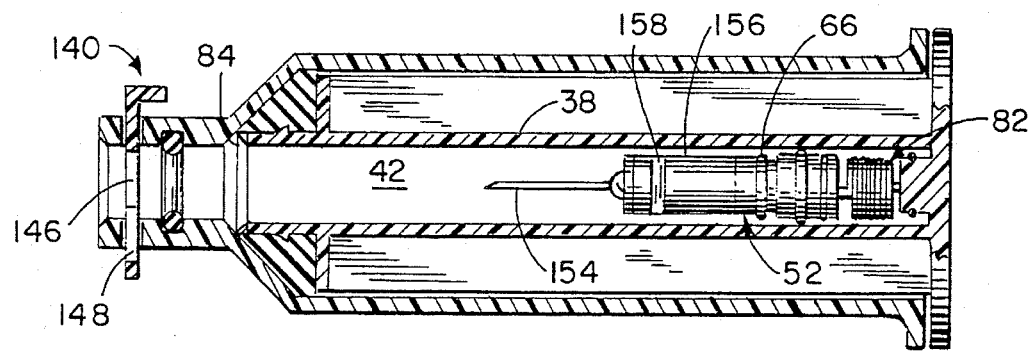
FIG. 8 is a view similar to FIG. 4, showing the actuator member moved to its release position for providing withdrawal of the needle assembly into the internal passageway defined by the plunger under the influence of the biasing means.

In operation, the embodiment of FIGS. 5–7 initially functions identically to the embodiment of FIGS. 1–4 as described previously. After retainer member head 54 is engaged within hub cavity 98, as shown in FIG. 6, the user continues forward movement of plunger 24 until a position as illustrated in FIG. 3 is attained, wherein retainer ring 84 is forced by end 40 of cylindrical wall 38 over ring 66, to release engagement of retraction member 52 with plunger 24. As before, this subjects retraction member 52 and hub 156 to the bias of spring 82, urging needle 154 rearwardly toward passage 42 defined by cylindrical wall 38. When it is desired to retract needle 154, the user manually engages his or her finger with actuator member engagement surface 142, and exerts a force thereon transverse to the longitudinal axis of barrel end wall 136, to move actuator member 140 to its release position in which the center of circular opening portion 146 is in alignment with the longitudinal axis of hub 156. Circular opening portion 146 is sized so as to release engagement between actuator member 140 and hub 156 when actuator member 140 is in its release position. This action releases engagement between barrel 132 and hub 156, and spring 82 then functions to withdraw retraction member 52, hub 156 and needle 154 into passageway 42, as illustrated in FIG. 8. As in the embodiment of FIGS. 1–4, this functions to disarm and prevent subsequent use of syringe assembly 130.

Figure 9:
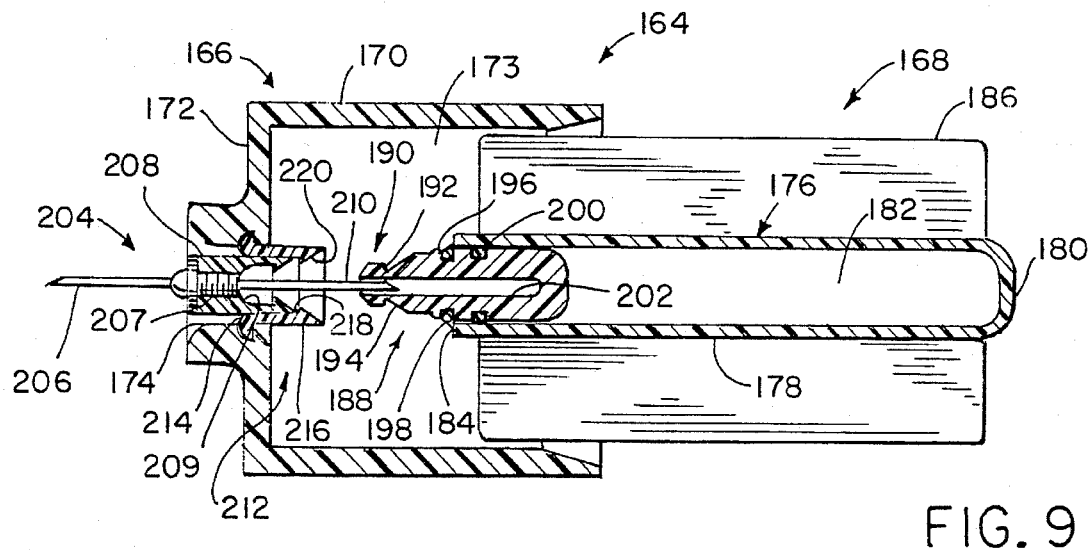
FIG. 9 is a longitudinal section view similar to FIGS. 1 and 5, showing another embodiment of an automatically retractable assembly constructed according to the invention.

FIG. 9 illustrates an embodiment of the invention incorporating a needle retraction mechanism similar to that of FIGS. 1–4 into a blood collection system. In this embodiment, a retractable needle blood collection system 164 includes a barrel-like cylindrical body 166 and a needle retrieving plunger assembly 168. Body 166 includes a side wall 170 and an end wall 172, which define an internal cavity 173. A central nipple is formed in end wall 172, defining a passage 174.

Plunger assembly 168 includes a central tube 176 having a side wall 178 and an end wall 180, and defining an internal passage 182. Side wall 178 terminates opposite end wall 180 in an annular end 184. A plunger outer body portion 186 is provided outwardly of central tube 176.

A retraction member 188 is mounted at the end of central tube 176 adjacent its annular end 184. Retraction member 188 includes a head 190 constructed similarly to head 54 in the embodiments of FIGS. 1–7, and defining a shoulder 192. Head 190 further defines a tapered actuator surface 194 and a rib 196, against which a retaining ring 198 is placed. Retaining ring 198 is engaged between rib 196 and annular end 184 of plunger tube side wall 178, for retaining retraction member 188 in its position as shown in FIG. 9. Retraction member 188 further includes a groove within which an O-ring 200 is seated, for providing a fluid-tight seal between central tube passage 182 and internal cavity 173 defined by syringe body 166. A central passage 202 is formed in retraction member 188, opening onto the forward surface of head 190 and extending rearwardly therefrom.

Passage 182 in plunger central tube 176 is evacuated. The vacuum behind retraction member 188 functions to bias retraction member 188 toward central tube end wall 180. Engagement of retaining ring 198 between central tube end 184 and rib 196 functions to retain retraction member 188 in its position as shown in FIG. 9 against the bias provided by the vacuum within passage 182.

A needle assembly 204 is located within passage 74 defined by the nipple formed in body end wall 172. Needle assembly 204 is similar in construction to needle assemblies 86, 152 illustrated in the embodiments of FIGS. 1–7, including a needle 206, a threaded stud 207, and a hub 208 constructed identically to hubs 90, 156 in the embodiments of FIGS. 1–4 and 5–7, respectively. Hub 208 includes an internally threaded passage and a hub cavity 209. A piercing needle 210 extends rearwardly from stud 207 to establish communication between body internal cavity 173 and the lumen of needle 206. In a manner as is known, piercing needle 210 is employed to pierce the membrane of an evacuated tube (not shown) for withdrawing blood from a patient after needle 206 is inserted into a blood vessel.

A retainer member 212 is engaged with hub 208 in the same manner as retainer member 108 in the embodiment of FIGS. 1–4, for retaining needle assembly 204 in its FIG. 9 position. Retainer member 212 includes an annular base 214 received within an internal groove formed in passage 174, and a series of rearwardly extending fingers 216. Each finger 216 defines a shoulder 218 and a tapered engagement surface 220.

In operation, the embodiment of FIG. 9 functions as follows. Needle 206 is first engaged with body 166 by threading stud 207 into the internally threaded passage of hub 208. The user then inserts needle 206 into a blood vessel, and withdraws blood from the patient by inserting an evacuated tube (not shown) into body cavity 173 such that piercing needle 210 punctures the membrane of the evacuated tube, in a manner as is known. The vacuum within the evacuated tube draws blood through needle 206 and piercing needle 210 into the evacuated tube. When the user has completed drawing blood from the patient, needle retrieving plunger assembly 168 is then inserted into body cavity 173 in a right-to-left direction. During such movement of plunger assembly 168, piercing needle 210 is received within internal passage 202 of retraction member 188. As right-to-left movement of plunger assembly 168 continues, head 190 of retraction member 188 is engaged within hub cavity 209, in a manner similar to that shown in FIGS. 2, 3 and 6 in the embodiments of FIGS. 1–4 and 5–7, respectively. When retraction member 188 is in this position, its actuator surface 194 engages tapered surfaces 220 of fingers 216, to flex fingers 216 outwardly in a manner similar to that shown and described with respect to fingers 122 in FIGS. 2 and 3. With fingers 216 in this position, engagement between hub 208 and body 164 is released. Additional right-to-left movement of plunger 168 results in end 184 of central tube side wall 178 forcing retaining ring 198 over rib 196 of retraction member 188, to release engagement between retraction member 188 and plunger 168. When this occurs, the vacuum within passage 182 functions to draw retraction member 188 and needle assembly 204 into passage 182, to simultaneously withdraw needle 206 from the patient's blood vessel and to disarm blood collection system 164. Passage 182 has a length sufficient to harbor needle 206 therewithin, to disarm syringe system 164 and to prevent subsequent reuse. Passage 202 in retraction member 188 is provided with a length sufficient to receive the entire length of piercing needle 210 during forward movement of plunger 168 relative to body 166.

Figure 10:
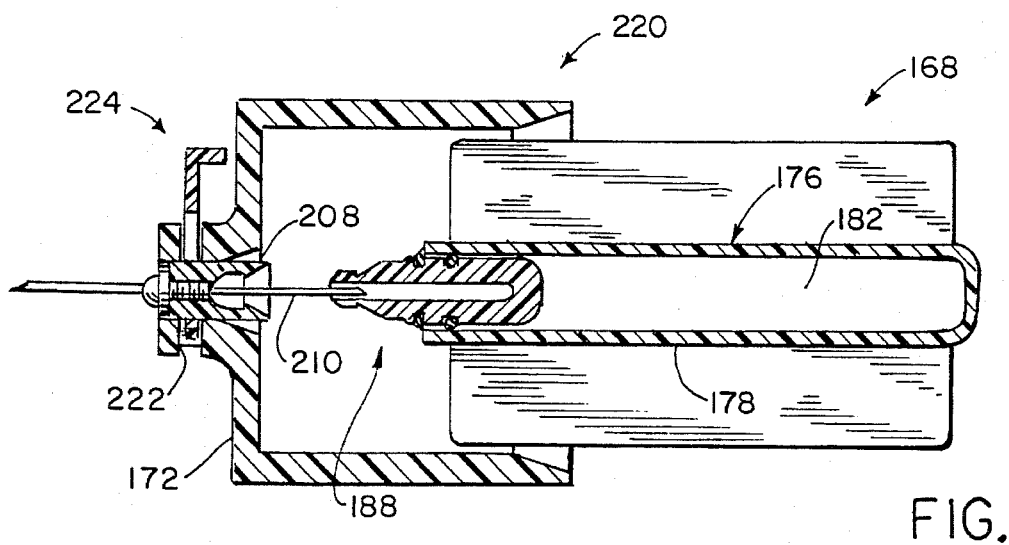
FIG. 10 is a longitudinal section view similar to FIG. 9, showing another embodiment of a manually operable retractable assembly constructed according to the invention.

FIG. 10 illustrates a manually actuated retractable needle blood collection system 220 somewhat similar to blood collection system 164 illustrated in FIG. 9. The FIG. 10 embodiment includes a plunger assembly and retraction member identical to that shown and described in the embodiment of FIG. 9, and like reference characters will be used to facilitate clarity. In addition, FIG. 10 includes a body, end wall and needle assembly substantially similar to that shown and described with respect to the embodiment of FIG. 9, and again like reference characters will be used to facilitate clarity.

In the FIG. 10 embodiment, the nipple formed in body end wall 172 defines a slot 222 within which a manually operated actuator member 224 is received. Actuator member 224 is constructed identically to actuator member 140 in the embodiment of FIGS. 5–7. Hub 208 is provided with slots within which the material of actuator member 224 is disposed when actuator member 224 is in its retaining position as shown in FIG. 10, for engaging hub 208 with body 166 of syringe system 220. As in the embodiment of FIGS. 5–7, manual downward movement of actuator member 224 after use of blood collection system 220 disengages actuator member 224 from hub 208, thus providing retraction of retraction member 188 and needle assembly 204 into central tube passage 182, in a manner similar to that described with respect to the embodiment of FIG. 9.

Yet another alternative form of the invention is illustrated in FIGS. 11–17. In this embodiment, a syringe assembly 230 generally includes a barrel 232 and a plunger 234. Barrel 232 includes a cylindrical side wall 236 defining an internal cavity 238, and a frustoconical end wall 240 which defines a tapered central passage 242 extending between cavity 238 and the exterior of end wall 240.

A sleeve, shown generally at 244, is received within passage 242 for mounting sleeve 244 to barrel 232. Sleeve 244 includes an end tip 246 defined by a tapered side wall 248 and an end wall 250, which defines a central opening 252 communicating between the exterior of tip 246 and an internal passage 254 defined by side wall 248 in combination with end wall 250.

Sleeve 244 further includes a tubular portion 256 extending rearwardly from tip 246, with a shoulder 258 defined therebetween. Tubular portion 256 includes a side wall 260 having a circular cross-section and a continuous linear outer surface. The inner surface of side wall 260 includes a pair of circumferential shoulders 262, 264, which define steps in the passage, shown at 266, defined by tubular portion 256. Tip passage 254 and tubular portion passage 266 are in communication with each other.

The upper portion of tubular portion wall 260 is provided with a channel 268, the purpose of which will later be explained.

A series of transverse passages, two of which are shown at 270, 272, extend through tubular portion side wall 260 adjacent shoulder 258 and the inner surface defined by barrel end wall 240. With this arrangement, the passages, such as 270, 272, establish communication between barrel cavity 238 and passage 266 defined by sleeve tubular portion 256.

A hub member 272 is mounted within sleeve 244. Hub member 272 includes a forward needle-receiving portion having a series of resilient fingers 274, each of which terminates in an inwardly extending hook 276. Fingers 274 define a tapered recess 278, which is adapted to receive a needle head 280 having a correspondingly tapered external surface 282. Needle head 280 further defines an annular shoulder 284. A needle 286 defining a lumen 288 is received within an internal passage defined by needle head 280, which further defines a passage 290 establishing communication between needle lumen 288 and the end of needle head 280.

With this construction, the needle assembly, consisting of needle head 280 and 286, is engaged with hub member 272 just prior to use of syringe assembly 230. The needle assembly is selected from a variety of similarly constructed needle assemblies having differently sized needles, and the operator selects the appropriately sized needle for the application in which syringe assembly 230 is to be used. The operator inserts needle head through opening 252 in end wall 250 of sleeve tip 246, to engage needle head external surface 282 with hooks 276 and fingers 274 of hub member 272. Continued insertion of needle head 280 results in fingers 274 deflecting outwardly until needle head 280 is in its FIG. 11 position, in which shoulder 284 has passed hooks 276. With needle head 280 in this position, fingers 274 deflect back inwardly toward each other, to engage hooks 276 with shoulder 284 to positively retain needle head 282 within hub member recess 278 and to prevent subsequent removal of the needle assembly. Alternatively, of course, it is understood that a threaded connection, similar to that disclosed in FIGS. 1–10, could be employed to secure the needle to hub member 272.

Hub member 272 further includes a series of passages, such as shown at 292, 294, which are aligned with the passages, such as 270, 272, formed in sleeve side wall 260, to establish communication between barrel cavity 238 and a central passage 296 formed in hub member 272. Central passage 296 in turn is in communication with passage 290 formed in needle head 280. In this manner, when hub member 272 is in its FIG. 11 position, communication is established between barrel cavity 238 and needle lumen 288.

O-rings, such as shown at 298, 300, are fitted within circumferential grooves formed in hub member 272. O-rings 298, 300 provide a fluid-tight seal between hub member 272 and sleeve 244 on either side of the passages, such as 292, 294, in hub member 272, and the passages, such as 270, 272, in sleeve side wall 260.

The rearward end of hub member 272 is provided with an outwardly extending annular lip 302. A spring 304 is positioned between lip 302 and shoulder 262 formed in the inner surface of sleeve side wall 260.

Figure 11:
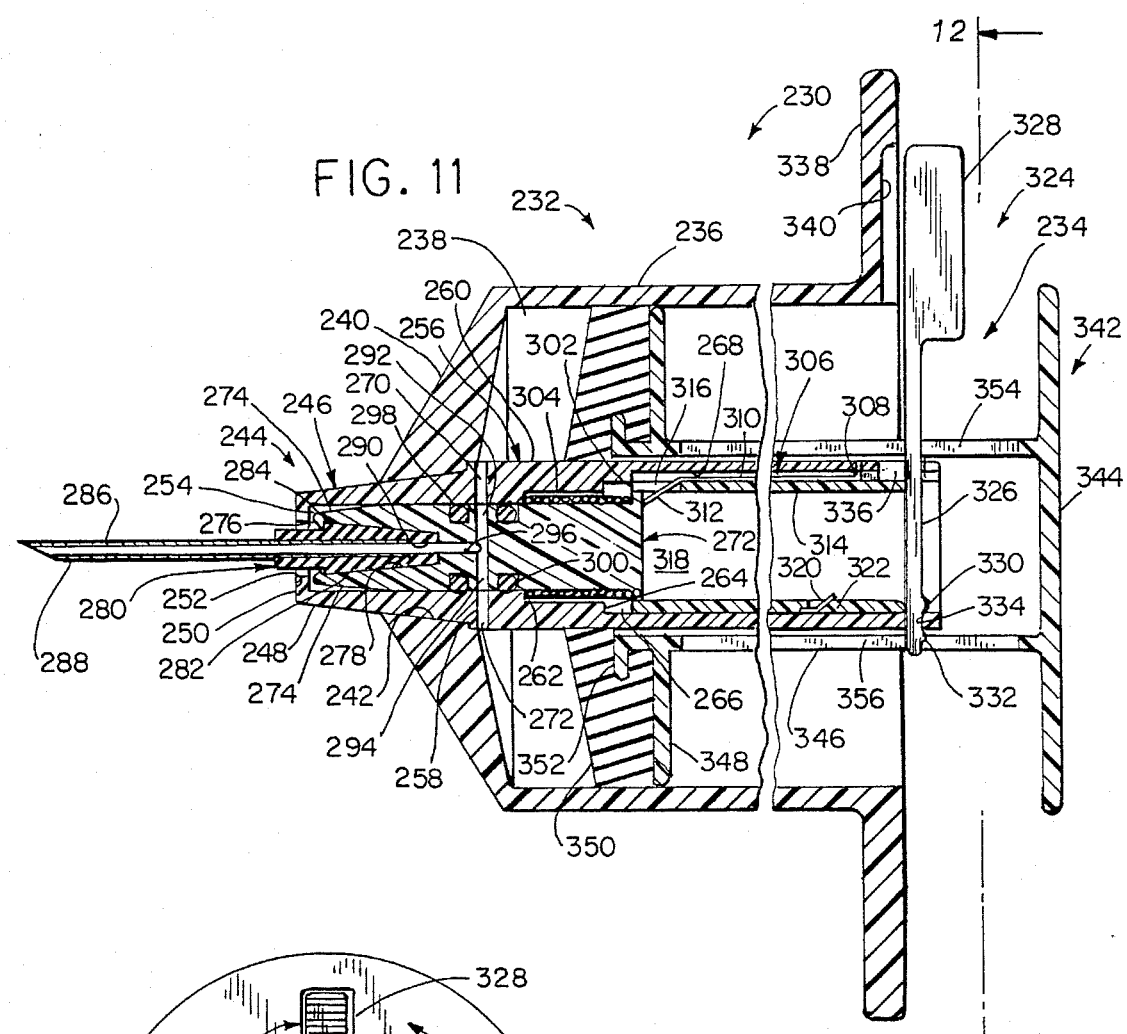
FIG. 11 is a longitudinal cross-sectional view of a syringe incorporating another embodiment of the needle retraction apparatus and method of the invention, showing the needle assembly and hub member retained in their extended position.
Figure 13:
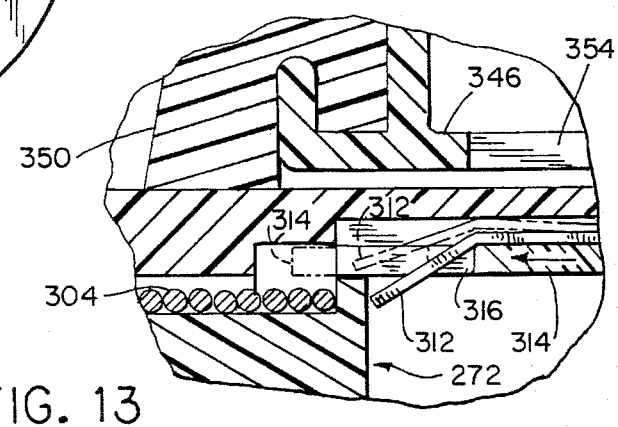
FIG. 13 is an enlarged partial section view of a portion of the syringe of FIG. 11, showing the releasable retainer mechanism for maintaining the hub member in a position in which the needle is in its armed condition.

A releasable retainer mechanism is interposed between sleeve 244 and hub member 272 for releasably retaining hub member 272 in its FIG. 11 position. Referring to FIGS. 11 and 13, the releasable retainer mechanism includes a retainer member 306 having a transverse rear end section 308 received within an opening formed in sleeve side wall 260 for maintaining retainer member 306 in a fixed longitudinal position relative to sleeve side wall 260. Retainer member 306 further includes a longitudinally extending middle section 310, and an inwardly bent forward end section 312, the end of which engages the rearward surface of hub member 272. Longitudinal middle section 310 of retainer member 306 is received within channel 268 formed in the internal surface of sleeve side wall 260.

An actuator tube 314 is mounted for longitudinal movement within the internal passage 266 defined by sleeve side wall 260. Actuator tube 314 includes a slot 316 within which the forward end section of retainer member 306 is received. Actuator tube 314 defines an internal passage 318, and the rearward end of hub member 272 is engaged within the forward end of passage 318. Actuator tube 314 further includes a resilient one-way lock member 320, the outer end of which extends into passage 318 through an opening 322 formed in the side wall of actuator tube 314.

Figure 12:
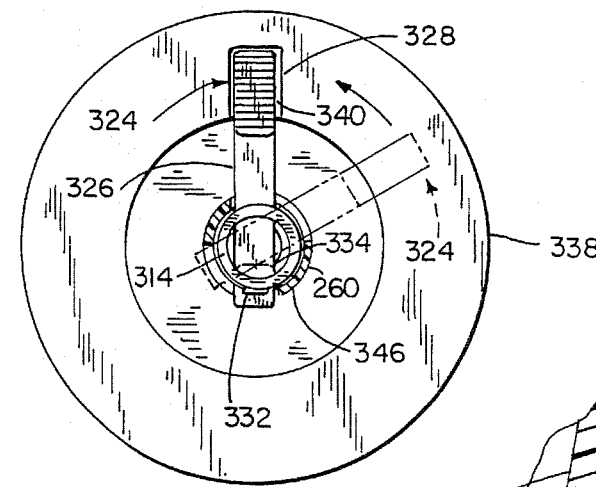
FIG. 12 is an end elevation view, reference being made to line 12—12 of FIG. 11, showing the manually operated actuator mechanism for the syringe of FIG. 11.

A manually operable triggering lever 324 is pivotably mounted to the rearward end of sleeve 244 for selectively moving actuator tube 314 between its positions as shown in FIGS. 11 and 12, in a manner to be explained. Triggering lever 324 includes a mounting stem 326 and a finger-actuable outer trigger portion 328. A pair of spaced protrusions 330, 332 are provided at the end of mounting stem 326 opposite trigger portion 328, and are engaged with the inner and outer surfaces, respectively, of sleeve side wall 260, with the portion of mounting stem 326 located therebetween being disposed within an opening 334 formed in sleeve side wall 260. Between protrusion 330 and trigger portion 328, mounting stem 326 extends through a slot 336 formed in sleeve side wall 260 opposite opening 334.

Referring to FIGS. 11 and 12, lever 324 is pivotable relative to the longitudinal axis of sleeve 244 between an inoperative position, shown in phantom in FIG. 12, and an operative position shown in solid lines in FIG. 12. Opening 332 and slot 336 are configured so as to allow such pivoting movement of lever 324 between its inoperative and operative positions.

As shown in FIGS. 11 and 12, syringe barrel 232 terminates at its outer end in a flange 338. Flange 338 includes a depression 340 disposed below trigger portion 328 of lever 324 when lever 324 is in its operative position.

Figure 14:
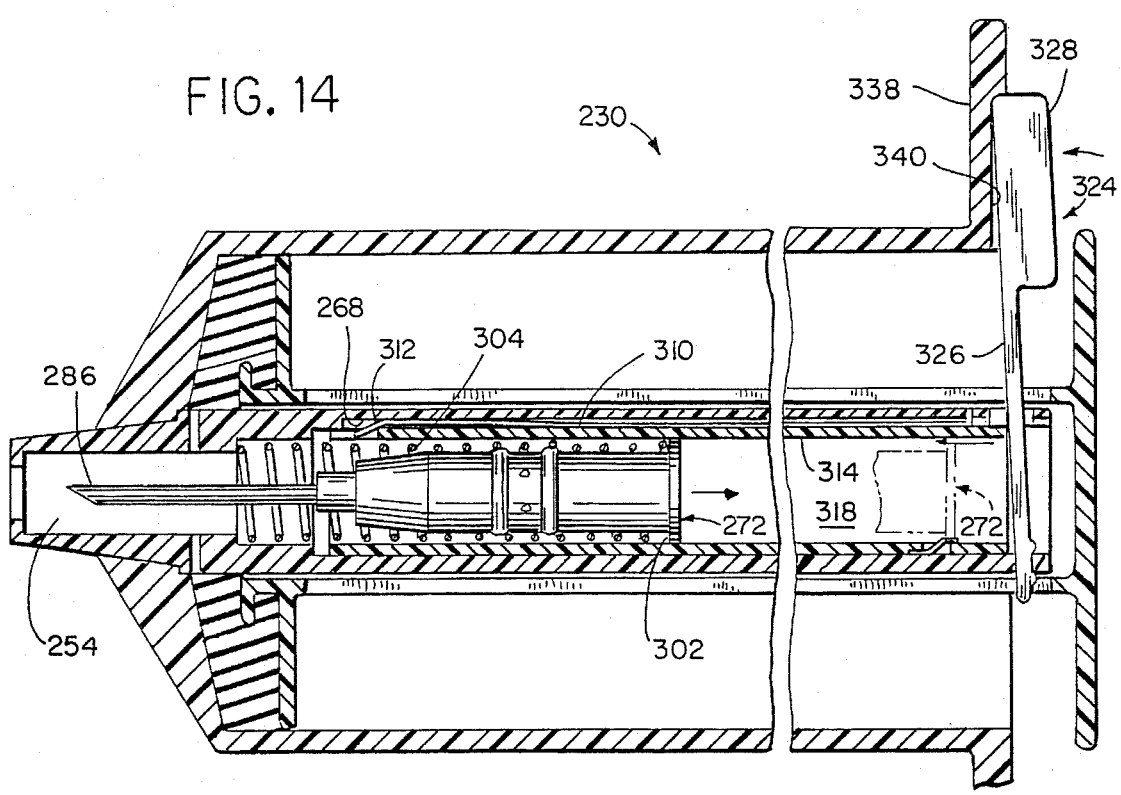
FIG. 14 is a longitudinal cross-sectional view similar to FIG. 11, showing actuation of the manually operated actuator mechanism for moving the releasable retainer mechanism to its release position to withdraw the hub member, and thereby the needle assembly, into the sleeve.
Figure 15:
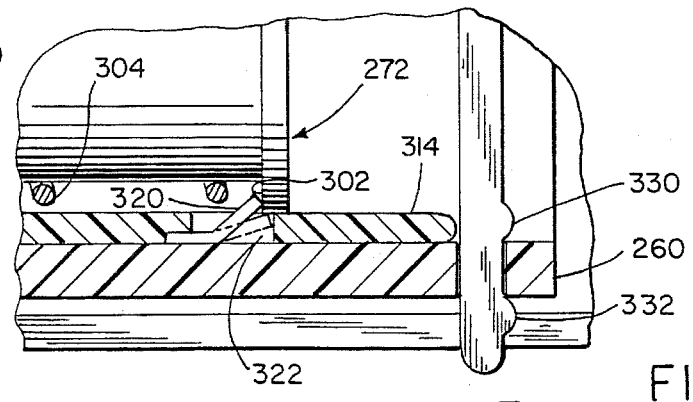
FIG. 15 is an enlarged partial sectional view illustrating the one-way retainer mechanism for retaining the hub member in position at the second end of the sleeve once the syringe assembly has been disarmed.

Lever 324 is pivotable between its positions shown in FIGS. 11 and 14 about a pivot point defined between protrusions 330, 332 at the point of connection between mounting stem 326 and sleeve side wall 260. When lever 324 is in any position other than in its operative position as shown in FIG. 12, lever 324 cannot be depressed due to engagement of the forward surface of trigger portion 328 with the rearward surface of barrel flange 338. However, when lever 324 is moved to its operative position as shown in FIG. 12, trigger portion 328 is movable into depression 340 so as to provide pivoting movement of lever 324 to its FIG. 14 position.

As shown in FIG. 11, a plunger assembly 342 is slidably mounted within barrel cavity 238. Plunger assembly 342 includes a plunger having a thumb plate 344, a tubular side wall 346, and an inner end ring 348. A resilient plunger head 350 is mounted to the forward end of the plunger, and is retained in place by a ring 352 located forwardly of ring 348 and disposed within a mating annular recess formed in head 350. Plunger side wall 346 includes a pair of longitudinal slots 354, 356 through which mounting stem 326 of trigger member 324 extend, to allow plunger 342 to be moved longitudinally relative to barrel 232 without interference from stem 326.

Referring to FIGS. 11–15, syringe assembly 230 functions as follows. First, as described previously, the operator selects an appropriate size of needle 286, having an associated head 280, and mounts the needle assembly to the forward end of hub member 272 as described previously. A sheath or the like is placed over needle 286 while the needle assembly is being installed, and is subsequently removed to expose the sharpened end of the needle. With lever 324 in its inoperative phantom line position of FIG. 12, the operator inserts the needle in a desired location into the patient, and depresses plunger assembly 342 using thumb plate 344 to eject the fluid contained within barrel cavity 238 into the patient through needle lumen 288. When as much of the fluid as desired has been injected into the patient, the user moves lever 324 to its operative solid line position as shown in FIG. 12, to position trigger portion 328 over depression 340. The user then uses his or her thumb or finger to engage trigger portion 328 and depress lever 324, in a manner as shown in FIG. 14, into depression 340. Alternatively, thumb plate 344 and lever 324 may be constructed such that, when plunger assembly 342 is in its full-forward position, thumb plate 344 engages trigger portion 328 to depress lever 344. This causes pivoting movement of lever 324, which results in axial forward movement of actuator tube 314 relative to sleeve 244. The forward end of actuator tube 314 engages the inwardly bent forward section 312 of retainer member 306, to move the end of retainer member 306 out of engagement with hub member 272. This movement of retainer member 306 to its release position results in spring 304 propelling hub member 272 rearwardly within passage 318 defined by actuator tube 314, to thereby withdraw needle 286 and its sharpened tip into passage 266 defined by sleeve 244. This disarmed condition of syringe assembly 230 is illustrated in FIG. 14. Spring 304 continues to propel hub member 272 rearwardly such that hub member lip 304 passes over one-way lock member 320, which flexes outwardly to allow passage of hub member lip 302 thereover. Lock member 320 then returns to its original position due to its resiliency, and engages the forward surface of lip 302 to subsequently prevent hub member 272 from moving forwardly within actuator tube passage 318. This prevents subsequent reuse of syringe assembly 232.

The above steps in withdrawing needle 286 can be undertaken either before or after needle 286 has been withdrawn from the patient.

As can be appreciated, syringe assembly 230 can be operated to withdraw needle 286 whether or not all of the fluid contained within barrel cavity 238 has been ejected by forward movement of plunger assembly 342.

Figure 16:
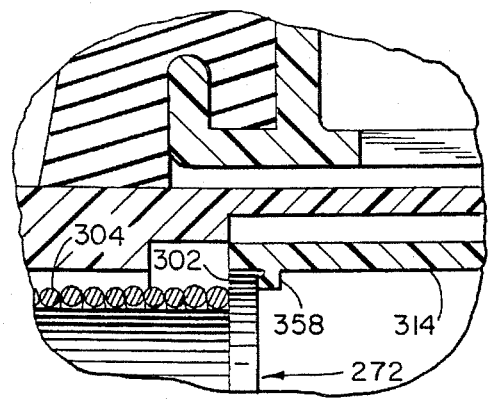
FIG. 16 is an enlarged partial sectional view similar to FIG. 13, showing an alternative embodiment for the releasable retainer mechanism for retaining the hub member in position adjacent the first end of the sleeve.
Figure 17:
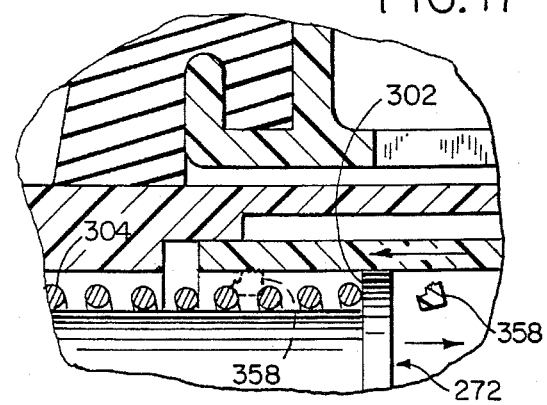
FIG. 17 is a view similar to FIG. 16, showing the manner in which the releasable retainer mechanism of FIG. 16 is moved to its release position to allow the hub member to be withdrawn into the sleeve.

FIGS. 16 and 17 illustrate an alternative retainer arrangement for releasably retaining hub member 272 in its forward position. Like reference characters will be used where possible to facilitate clarity. As shown in FIG. 16, a frangible retainer element 358 is formed integrally with actuator tube 314, extending inwardly from the inner wall defined by actuator tube 314. Retainer element 358 has sufficient strength to maintain hub member 272 in its forward position during use of syringe assembly 230 while plunger assembly 342 is operated to eject fluid from barrel cavity 238. When lever 324 is moved to its FIG. 12 solid line position and depressed as shown in FIG. 14, actuator tube 314 again moves forwardly within sleeve passage 266, and such forward movement of actuator tube 314 functions to break frangible retainer element 358 away from actuator tube 314. This releases engagement between hub 272 and sleeve 244, resulting in spring 304 propelling hub member 272 rearwardly within passage 318 defined by actuator tube 314. Frangible retainer element 358 is used in place of retainer member 306 (FIGS. 11–14) to releasably maintain hub member 272 in its forward position. Alternatively, a frangible tab or ring element could be formed integrally with lip 302 of hub member 272 in place of frangible element 358.

FIGS. 18–23 illustrate yet another form of the invention. In this embodiment, a syringe assembly 370 generally includes a barrel 372 and a plunger 374. Barrel 372 includes a cylindrical side wall 376 defining an internal cavity 378, and an end wall 380 from which a nipple 382 extends. Nipple 382 defines a central passage 384 extending between cavity 378 and the exterior of syringe assembly 370. A flange 385 extends outwardly from the rear end of barrel side wall 376.

A sleeve member 386 extends through nipple passage 384 and is secured to barrel 372 by engagement of a flange 388 with the forward end of nipple 382. The forward portion of sleeve member 386 has a cross-section corresponding to that of nipple passage 384 which, in combination with flange 388, functions to securely mount sleeve member 386 to barrel 372.

Sleeve member 386 defines a cylindrical side wall 390 which extends axially throughout the length of barrel 372 and projects slightly from the rearward end thereof. Sleeve wall 390 includes a forward annular seat 392 and an internal shoulder 394. Sleeve 386 defines an axial passage 396 which extends throughout its entire length, with seat 392 and shoulder 394 providing a stepped configuration to passage 396.

A series of lateral passages such as 398 are formed in sleeve side wall 390, establishing communication between barrel cavity 378 and sleeve passage 396. A rearwardly opening slot 400 is formed in sleeve side wall 390 toward the rearward end of sleeve member 386.

A hub member 402 is mounted within sleeve member passage 396. As shown in FIGS. 18 and 19, hub member 402 includes a central ring section 404 defining a forward shoulder 406. A series of fingers 408 extend forwardly from ring section 404, with a slot such as 410 being located between adjacent fingers 408. Fingers 408 define a central passage 412.

The forward end portion of each finger 408 defines a rearwardly facing seat 416, which collectively cooperate to define a restriction in passage 412 opening onto the forward end of hub member 402. Fingers 408 are capable of being flexed outwardly from their normal at-rest position of FIGS. 18 and 19, and thereafter returning to their normal position.

Rearwardly of ring section 404, hub member 402 defines a series of flexible retainers 418 with slots 420 disposed between adjacent retainers 418. Retainers 418 are constructed similarly to fingers 408, and are capable of being flexed from their normal, at-rest position as illustrated in FIGS. 18 and 19.

Each retainer 418 is provided at its rearward end with an outwardly ramped actuator surface 422 which extends between the rearward end of hub member 402 and the axial outer surface of its associated retainer 418.

A needle assembly 424 is engageable with hub member 402. Needle assembly 424 includes a hollow needle 426 defining a lumen, and a needle head 428 to which the rear portion of needle 426 is secured. Needle head 428 includes a forward portion defining a forwardly-opening passage within which the rear portion of needle 426 is received, and a rearwardly extending passage 430 which establishes communication between the lumen of needle 426 and a cross-passage 432 which opens onto opposite sides of head 428. The rearward portion of head 428 includes a conical retainer member 434 defining an annular engagement surface 436, and a neck 438 disposed between engagement surface 436 and a shoulder 437.

A pair of mirror-image modified O-rings 440, 442 are disposed within sleeve passage 396 adjacent seat 392. The forward end of front O-ring 440 engages seat 392, and the forward end of O-ring 442 engages the rearward end of O-ring 440. A washer 444 engages the rearward end of rear O-ring 442, so as to secure O-rings 440, 442 as a "cartridge" within sleeve passage 396.

Slots, such as 446, are formed in the engaging ends of O-rings 440, 442 extending between the outside and inside of each, so as to provide fluid communication between barrel cavity 378 and the lumen of needle 426 via sleeve passages 398, slots 446, cross-passage 432 in head 428, and longitudinal passage 430 extending between cross-passage 432 and the needle lumen. O-rings 440, 442 engage head 428 on either side of cross-passage 432 to provide a fluid-tight seal between head 428 and the inner surface of sleeve side wall 390.

A spring 448 bears between the rearward surface of washer 444 and shoulder 406 defined by hub ring section 404, so as to urge hub member 402 rearwardly.

An actuator 450 is mounted to sleeve member 386 within the rear portion of sleeve passage 396. Actuator 450 includes an actuator tube 452 having a cylindrical side wall 454 and an end wall 456. Side wall 454 terminates in a forward end 458 which engages the rear ends of hub member retainers 418, so as to retain hub member 402 in its forward position of FIG. 18, in which needle 426 is maintained by hub member 402 in its outwardly extending, armed condition. Actuator tube 452 defines a forwardly-opening passage 460, and actuator tube side wall 454 includes an inwardly deformed tab 462 oriented such that its rear end extends into passage 460. Side wall 454 further defines an outwardly deformed tab 464 having a rear end portion which extends into a slot 466 formed in sleeve member 386. Slot 466 extends throughout an arc of sleeve side wall 390, with engagement of tab 464 with the ends of slot 466 defining a range of rotational movement of actuator tube 452 relative to sleeve member 386.

Actuator member 452 includes a trigger 468 extending laterally from the rear end of actuator tube 452 through slot 400 formed in sleeve side wall 390.

A plunger assembly 470 is movably mounted within barrel cavity 378. Plunger assembly 470 includes a resilient plunger head 472 having an annular outer edge which establishes fluid-tight engagement with the inner surface of barrel side wall 376, and a central passage engageable with the outer surface of sleeve side wall 390 and establishing a fluid-tight seal therewith. Plunger assembly 470 further includes a plunger having a cylindrical side wall 474 extending forwardly from a thumb plate 476.

Plunger side wall 474 includes a slot 478 through which trigger 468 extends, and which also accommodates assembly of actuator 450 to sleeve 386. Referring to FIG. 20, slots 400, 478 accommodate pivoting movement of trigger 468 between an operative position (at approximately twelve o'clock) and an inoperative position (at approximately two o'clock). In the operative position, trigger 468 is positioned over a recess 480 formed in flange 385 at the rearward end of barrel 372, which allows trigger 468 to be depressed, i.e. moved longitudinally in a forward direction relative to barrel 372. When trigger 468 is in its inoperative, phantom line position, trigger 468 is moved out of alignment with recess 480 such that the material of flange 385 prevents trigger 468 from being moved forwardly relative to barrel 372, thus preventing movement of actuator tube 452 forwardly of its retaining position of FIG. 18.

In operation, syringe assembly 370 of FIGS. 18-23 functions as follows. As in the other embodiments of the invention, the user first selects the appropriate needle assembly 424 according to the application in which syringe assembly 370 is to be used, i.e. selecting a needle assembly having an appropriate size of needle 426 as desired. With the cap (not shown) in place over needle 426, the user mounts needle assembly 424 to syringe assembly 372 by inserting needle head 428 into sleeve passage 396 from the forward end of sleeve member 386, using an axial push-on force. Needle head 428 engages and passes over O-rings 440 and 442 until the angled surface of retainer member 434 engages fingers 408. The user continues application of the axial push-on force, and retainer member 434 flexes fingers 408 outwardly until engagement surface 436 passes seats 416 defined by fingers 408. Fingers 408 then return to their position as shown in FIGS. 18 and 21-23, in which seats 416 engage engagement surface 436 so as to prevent needle assembly 424 from being moved forwardly relative to sleeve member 386 and barrel 372. Shoulder 437 is engaged by the forward ends of fingers 408, so as to prevent relative axial rearward movement of needle head 428 relative to sleeve member 386 and barrel 372.

If the user is injecting a fluid from barrel cavity 378 into a patient, the user then engages thumb plate 476 with his or her thumb and pushes plunger assembly 470 forwardly relative to barrel 372, resulting in passage of the fluid from barrel cavity 378 through sleeve passages 398 and O-ring slots 446 into needle head cross-passage 432 and axial passage 430, and into the lumen of needle 426 for injection into the patient. If the user is withdrawing fluid from a patient, the user engages thumb plate 476 to draw plunger assembly 470 rearwardly, resulting in reverse operation so as to draw fluid from the patient into barrel cavity 378.

When fluid is being injected into the patient, syringe assembly 370 automatically disarms itself after all of the fluid is ejected from barrel cavity 378. As shown in FIG. 21, in which plunger assembly 470 is in its full-forward position, the rear edge of plunger side wall 474 defining slot 478, shown at 482, engages the rear surface of trigger 468 so as to move trigger 468 into recess 480 and to thereby move actuator tube 452 to a release position in which actuator tube forward end 458 engages shoulder 394 formed in the internal surface of sleeve passage 396. During such forward movement of actuator tube 452, ramped actuator surfaces 422 of flexible retainers 418 engage shoulder 394 so as to flex the outer ends of retainers 418 inwardly to a release position as shown in FIG. 21, thus releasing engagement of retainers 418 with the forward end of actuator tube 452. As shown in FIG. 22, spring 448 then functions to propel hub member 402 rearwardly into actuator tube passage 460, which draws needle assembly 424 rearwardly into and through sleeve passage 396 so as to enclose the sharpened end of needle 426 within sleeve passage 396. During such rearward movement of hub member 402, retainers 418 pass over inwardly extending tab 462, which prevents subsequent forward movement of hub member 402 even if spring 448 were disabled. Otherwise, spring 448 functions to at all times retain hub member 402 in a rearward position as in FIG. 22 in which needle 426 is fully enclosed.

Alternatively, as illustrated in FIG. 23, the user can depress trigger 468 at any time, regardless of the position of plunger assembly 470, so as to withdraw needle assembly 424 and to disable syringe assembly 370. The user accomplishes this by simply engaging his or her thumb or finger with trigger 468 so as to depress trigger 468 into recess 480, which again moves flexible retainers 418 out of engagement with forward end 458 of actuator tube 452 as described previously so as to enable spring 448 to move hub member 402 rearwardly into actuator tube passage 460 and to enclose needle 426 within sleeve passage 396.

If the user wishes to ensure that needle 426 is retained in its extended, armed condition and to disable the retraction mechanism of the invention, the user pivots trigger 468 to its inoperative position, as shown in phantom in FIG. 20, in which the material of flange 377 prevents trigger 368 from being depressed. This functions as a "safety" in order to ensure that trigger 468 can only be depressed when desired.

While the invention as shown in FIGS. 11–23 has been described as a syringe assembly, it is understood that the illustrated assembly could also be used as a device for withdrawing a body fluid from a patient, with actuation of the mechanism to withdraw needle 286 occurring after a desired amount of fluid has been withdrawn from the patient.

Various alternatives and embodiments are contemplated as being within the scope of the following claims particularly pointing out and distinctly claiming the subject matter regarded as the invention.

We claim:

1. A medical assembly, comprising:

a barrel having an internal cavity extending along a longitudinal axis;

a plunger assembly adapted for longitudinal sliding movement within the barrel cavity;

a sleeve mounted to the barrel, the sleeve defining a forward end and a rearward end and an internal passage extending therebetween;

a hub member mounted within the sleeve in a first position toward the forward end of the sleeve;

a needle mounted to the hub member, the needle defining a lumen;

passage means interposed between the needle lumen and the barrel cavity for establishing communication therebetween;

bias means for urging the hub member toward the rearward end of the sleeve;

a releasable retainer mechanism engageable with the hub member for retaining the hub member in its first position against the force of the bias means and movable to a release position for disengaging the hub member; and a trigger for selectively moving the releasable retainer mechanism to its release position in response to either engagement of the plunger assembly with the trigger or manual engagement with the trigger by a user regardless of the position of the plunger, wherein engagement of the hub member is released and the bias means functions to draw the hub member rearwardly to withdraw the needle into the internal passage defined by the sleeve.

2. The medical assembly of claim 1, wherein the needle extends from a needle head engageable with the hub member by means of mating connection structure interposed between the hub member and the needle head, wherein the needle head is engageable with the hub member by application of a push-on force to the needle head.

3. The medical assembly of claim 1, wherein the releasable retainer mechanism includes an actuator member movably mounted to the sleeve, wherein the trigger is associated with the actuator member, and wherein the hub member includes one or more flexible retainers engageable with the actuator member for retaining the hub member in its first position, wherein the flexible retainers are movable out of engagement with the actuator member when the actuator member is moved so as to place the releasable retainer mechanism in its release position.

4. The medical assembly of claim 3, wherein the sleeve includes release structure engageable with the flexible retainers when the releasable retainer mechanism is moved to its release position for moving the flexible retainers out of engagement with the actuator member.

5. The medical assembly of claim 1, wherein the plunger is engageable with the trigger so as to move the releasable retainer mechanism to its release position when the plunger attains a predetermined position relative to the barrel.

6. The medical assembly of claim 5, wherein the plunger defines a passage through which the sleeve extends such that the plunger is movable relative to the sleeve, and wherein the releasable retainer mechanism includes an actuator member defining an internal passage and disposed within the sleeve, wherein the trigger is mounted to the actuator member.

7. The medical assembly of claim 6, wherein the trigger extends transversely through a slot formed in a wall of the plunger, and wherein an edge of the slot is engageable with the trigger when the plunger reaches a predetermined position relative to the barrel so as to move the actuator member to place the releasable retainer mechanism in its release position.

8. The medical assembly of claim 7, wherein the trigger is rotationally movable between an operative position in which the trigger is capable of being depressed and an inoperative position in which the trigger is incapable of being depressed so as to prevent the releasable retainer mechanism from being moved to its release position.

9. A medical assembly, comprising:

a barrel having an internal cavity extending along a longitudinal axis;

a plunger assembly adapted for longitudinal sliding movement within the barrel cavity;

a sleeve mounted to the barrel, the sleeve defining a forward end and a rearward end and an internal passage extending therebetween;

a hub member mounted within the sleeve in a first position toward the forward end of the sleeve;

a needle mounted to the hub member, the needle defining a lumen;

passage means interposed between the needle lumen and the barrel cavity for establishing communication therebetween;

bias means for urging the hub member toward the rearward end of the sleeve;

an actuator movably mounted to the sleeve for movement between a retaining position and a release position, the actuator including a trigger member; and wherein the hub member includes one or more flexible retainers engageable with the actuator for retaining the hub member in its first position when the actuator is in its retaining position; and structure for moving the flexible retainers out of engagement with the actuator member upon movement of the actuator to its release position for enabling the bias means to draw the hub member rearwardly to withdraw the needle into the internal passage defined by the sleeve.

10. The medical assembly of claim 9, wherein the trigger extends transversely through a slot defined by a wall of the plunger, and wherein the actuator comprises a tubular member movably mounted within the internal passage of the sleeve.

11. The medical assembly of claim 10, wherein the trigger member is engageable by the plunger upon movement of the plunger to a predetermined position relative to the barrel for moving the actuator from its retaining position to its release position, and wherein the trigger is also manually engageable by a user for movement from its retaining position to its release position regardless of the position of the plunger relative to the barrel.

12. The medical assembly of claim 11, wherein the trigger member is engageable by an edge of the plunger defining a slot through which the trigger member extends for moving the actuator to its release position upon movement of the plunger to a predetermined position relative to the barrel.

13. The medical assembly of claim 9, wherein the actuator is movably mounted within the internal passage of the sleeve and defines a forward end, wherein the one or more flexible retainers are engaged with the actuator forward end when the actuator is in its retaining position.

14. The medical assembly of claim 13, wherein the structure for moving the flexible retainers out of engagement with the actuator member comprises a shoulder formed on the sleeve, wherein the one or more flexible retainers each include a ramped actuator surface engageable with the shoulder upon movement of the actuator to its release position.

15. The medical assembly of claim 14, wherein the actuator comprises a tubular member mounted within the sleeve rearwardly of the shoulder, wherein movement of the actuator to its release position results in engagement of the actuator forward end with the shoulder.

16. The medical assembly of claim 14, wherein the ramped actuator surface extends between the shoulder and the forward end of the actuator when the actuator is in its retaining position.

17. A medical assembly, comprising:

a barrel having an internal cavity extending along a longitudinal axis;

a plunger assembly adapted for longitudinal sliding movement within the barrel cavity;

a sleeve mounted to the barrel, the sleeve defining a forward end and a rearward end and an internal passage extending therebetween;

a hub member mounted within the sleeve in a first position toward the forward end of the sleeve;

a needle mounted to the hub member, the needle defining a lumen;

passage means interposed between the needle lumen and the barrel cavity for establishing communication therebetween;

bias means for urging the hub member toward the rearward end of the sleeve;

an actuator movably mounted to the sleeve for movement between a retaining position and a release position;

a trigger for selectively moving the actuator to its release position in response to either engagement of the plunger assembly with the trigger or manual engagement of the trigger by a user regardless of the position of the plunger;

wherein the hub member includes one or more flexible retainers engageable with the actuator for retaining the hub member in a first position when the actuator is in its retaining position; and structure for moving the flexible retainers out of engagement with the actuator member upon movement of the actuator to its release position for enabling the bias means to draw the hub member rearwardly and to withdraw the needle into the internal passage defined by the sleeve.

* * * * *